(12) United States Patent
Zhang

(10) Patent No.: US 8,800,392 B2
(45) Date of Patent: Aug. 12, 2014

(54) DEFORMATION TESTING DEVICE

(75) Inventor: Bing-Jun Zhang, Shenzhen (CN)

(73) Assignees: Hong Fu Jin Precision Industry (ShenZhen) Co., Ltd., Shenzhen (CN); Hon Hai Precision Industry Co., Ltd., New Taipei (TW)

( * ) Notice: Subject to any disclaimer, the term of this patent is extended or adjusted under 35 U.S.C. 154(b) by 343 days.

(21) Appl. No.: 13/187,539

(22) Filed: Jul. 21, 2011

(65) Prior Publication Data

US 2012/0297898 A1 Nov. 29, 2012

(30) Foreign Application Priority Data

May 24, 2011 (CN) .......................... 2011 1 0135261

(51) Int. Cl.
*G01L 1/04* (2006.01)
(52) U.S. Cl.
USPC .................................................... 73/862.637
(58) Field of Classification Search
USPC .................................................... 73/862.637
See application file for complete search history.

(56) References Cited

U.S. PATENT DOCUMENTS 6,082,201 A * 7/2000 Ishikawa .......................... 73/849
2010/0307260 A1* 12/2010 Zhang .............................. 73/838

FOREIGN PATENT DOCUMENTS

TW 201100792 A1 1/2011

* cited by examiner

*Primary Examiner* — Lisa Caputo
*Assistant Examiner* — Brandi N Hopkins
(74) *Attorney, Agent, or Firm* — Novak Druce Connolly Bove + Quigg LLP

(57) ABSTRACT

A deformation testing device includes a base holding a workpiece and a testing machine arranged on the base. The testing machine includes a distance-measurement device and a force-applying device. The distance-measurement device includes a distance meter metering a moving distance of an elastic portion of the workpiece and includes a measurement probe. The force-applying device includes a force meter and a transmission member. The force meter slidably is mounted on the base and includes a force-applying post. The transmission member includes a first post and a second post secured to the first post. The first post is aligned with the force-applying post transmits a force from the force-applying post to the elastic portion. The measurement probe abuts against the second post. The force meter applies and measures a force acted upon the elastic portion through the force-applying post and the first post.

19 Claims, 5 Drawing Sheets

DEFORMATION TESTING DEVICE

BACKGROUND

1. Technical Field

The present disclosure relates to deformation testing devices.

2. Description of Related Art

Quality test is generally needed for a product before for sale. For example, a spring may be tested to obtain a diagram of indicative relationship between push forces (pressure) and deformation of the spring and of indicative relationship between pull forces and the deformation of the spring to determine whether the spring meets requirements. Therefore, what is needed is a deformation testing device.

DETAILED DESCRIPTION

Figure 1:
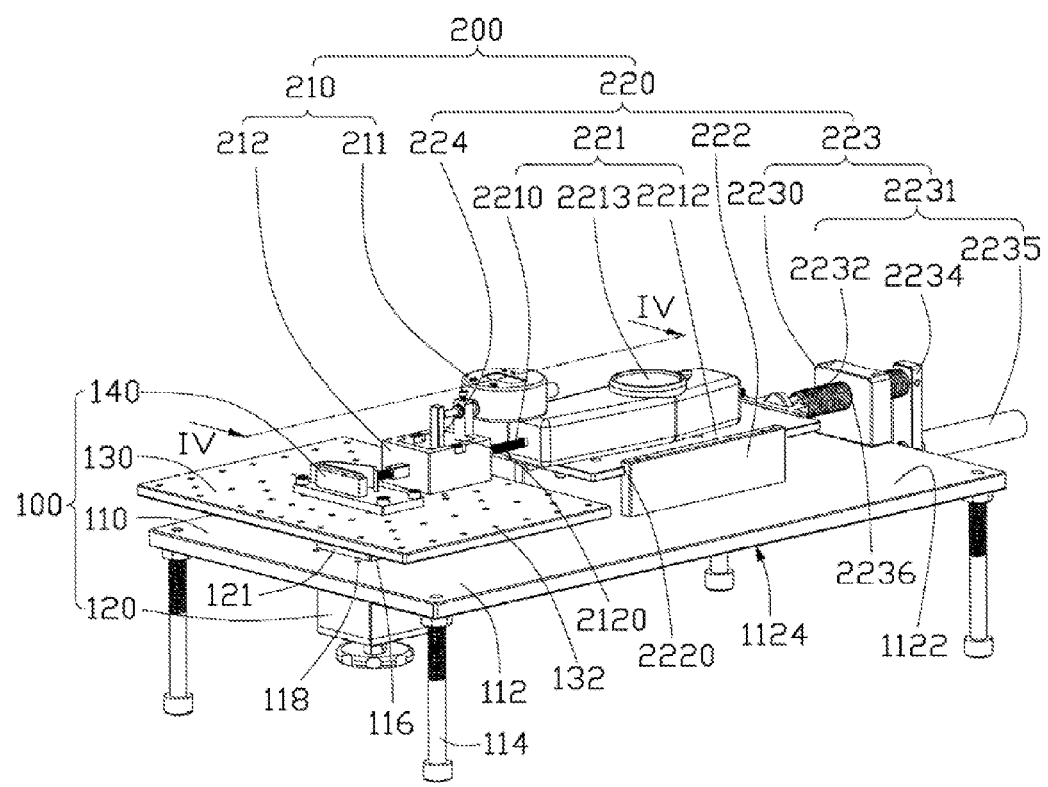
FIG. 1 is a schematic view of a deformation testing device including a position adjusting device, according to a first embodiment.

Embodiments of the present deformation testing device will now be described in detail and with reference to the drawings.

Referring to FIGS. 1 to 4, a deformation testing device 10, according to a first embodiment, includes a base 100 and a testing machine 200. The testing machine 200 is mounted on the base 100. The base 100 holds a workpiece 300. The testing machine 200 tests the deformation of the workpiece 300. In this embodiment, the workpiece 300 is a V-shaped elastic sheet and includes an elastic arm 302.

The base 100 includes a support 110, a position adjusting device 120, a platform 130 and a positioning device 140.

The support 110 includes a support plate 112 and four feet 114. The support plate 112 includes a top surface 1122 and a bottom surface 1124. The top surface 1122 and the bottom surface are located at opposite sides of the support plate 112. The four feet 114 are arranged at four corners of the support plate 112, respectively. The height of the support plate 112 can be adjusted by rotating the four feet 114. An insertion through hole 116 and a number of first threaded through holes 118 are defined in the support plate 112 and extend from the top surface 1122 of the support plate 112 to the bottom surface 1124 of the support plate 112. The first threaded through holes 118 are positioned adjacent to the insertion through hole 116.

Figure 2:
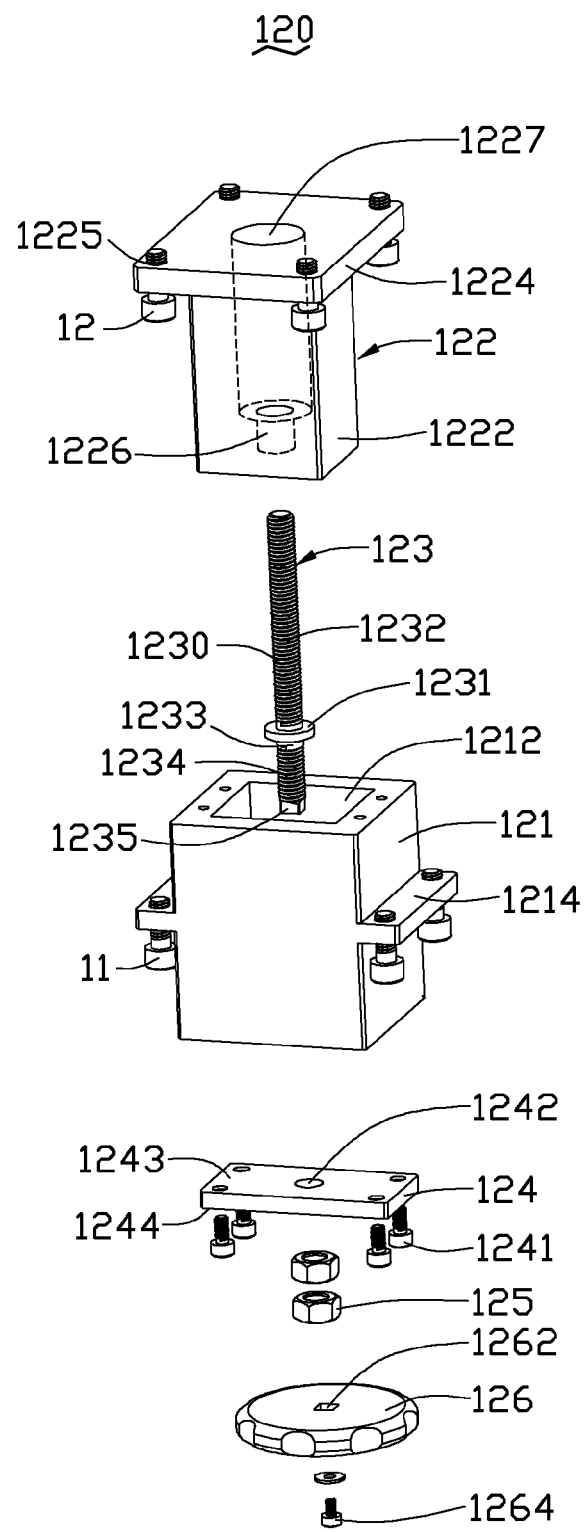
FIG. 2 is an exploded view of the position adjusting device of FIG. 1.

Referring to FIG. 2, the position adjusting device 120 includes an insertion body 121, a moveable platform 122, a first threaded post 123, a secured plate 124, two nuts 125 and a knob 126. Two protruding plates 1214 extend from opposite sides of the insertion body 121, respectively. The insertion body 121 extends through the insertion through hole 116. The two protruding plates 1214 are in contact with the bottom surface 1124 of the support plate 112 and are secured to the bottom surface 1124 of the support plate 112 with bolts 11. Therefore, the insertion body 121 is mounted to the support plate 112.

A first receiving space 1212 is defined through the top to the bottom of the insertion body 121. The moveable platform 122 includes an insertion portion 1222 and a mounting tray 1224 at a top end of the insertion portion 1222. The insertion portion 1222 is shaped and sized to be received in the first receiving space 1212 and can be moved along the first receiving space 1212. The mounting tray 1224 is positioned above the top surface 1122 of the support plate 112. Four second threaded through holes 1225 are defined in four corners of the mounting tray 1224, respectively. A second receiving space 1227 and a third threaded through hole 1226 are defined in that order through the top to the bottom of the moveable platform 122. The second receiving space 1227 is in communication with the third threaded through hole 1226.

The first threaded post 123 includes a post body 1230, and a flange 1231 mounted on the post body 1230. The post body 1230 includes a first threaded portion 1232, an even portion 1233, a second threaded portion 1234 and an engaging portion 1235 in that order from the top to the bottom of the post body 1230. The flange 1231 is located between the first threaded portion 1232 and the even portion 1233. The first threaded portion 1232 is screwed into the third threaded through hole 1226. The second threaded portion 1234 threadedly extends through the two nuts 125. The engaging portion 1235 is substantially a cuboid. A threaded blind hole (not shown) is defined at a distal end of the engaging portion 1235.

The secured plate 124 is mounted to the bottom of the insertion body 121 with bolts 1241. A first through hole 1242 is defined in the secured plate 124. The first through hole 1242 is aligned with the first receiving space 1212 and the third threaded through hole 1226. A diameter of the first through hole 1242 is slightly greater than those of the even portion 1233, the second threaded portion 1234 and the engaging portion 1235. The second threaded portion 1234 and the engaging portion 1235 pass through the first through hole 1242. The even portion 1233 is received in the first through hole 1242. The flange 1231 is against a top surface 1243 of the secured plate 124. The two nuts 125 threadedly sleeve the second threaded portion 1234. The upper nut 125 is against a bottom surface 1244 of the secured plate 124. Therefore, the secured plate 124 is sandwiched between the flange 1231 and the upper nut 125. Friction between the secured plate 124 and the flange 1231, and between the secured plate 124 and the upper nut 125 is strong enough to stop the first threaded post 123 when no operation is implemented but weak for the first threaded post 123 to be manually rotated.

The knob 126 is round-shaped. A central through hole 1262 is defined in the knob 126. The engaging portion 1235 is engaged in the central through hole 1262. A bolt 1264 is screwed into the threaded blind hole so that the knob 126 is secured to the first threaded post 123. The first threaded post 123 rotates as the knob 126 rotates. Under restriction of the flange 1231, the nut 125 and the secured plate 124, the first threaded post 123 cannot be moved along a longitudinal axis thereof when the first threaded post 123 rotates. Since the first threaded portion 1232 is screwed into the third threaded through hole 1226, rotation of the first threaded post 123 can cause up-or-down movement of the moveable platform 122 in the first receiving space 1212.

The platform 130 is substantially plate-shaped and substantially parallel to the support plate 112. A number of fourth threaded through holes 132 are defined in the platform 130. The platform 130 is secured to the mounting tray 1224 so that the platform 130 can move in unison with the moveable platform 122. For example, four bolts 12 may be used and each bolt 12 extends through the second threaded through hole 1225 and the corresponding fourth threaded through hole 132 to secure the platform 130 to the moveable platform 122. Therefore, a height of the platform 130 can be adjusted by rotating the knob 126 in a clockwise or counterclockwise direction.

Figure 3:
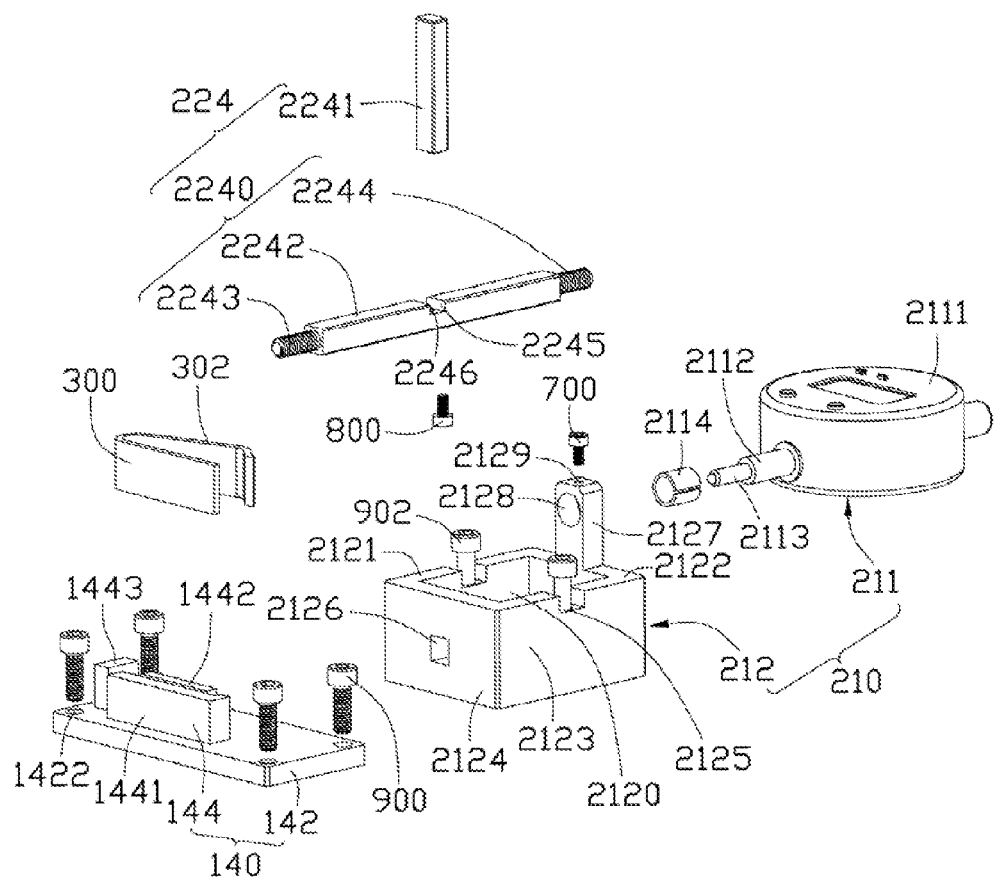
FIG. 3 is a partially exploded view of the deformation testing device of FIG. 1.
Figure 4:
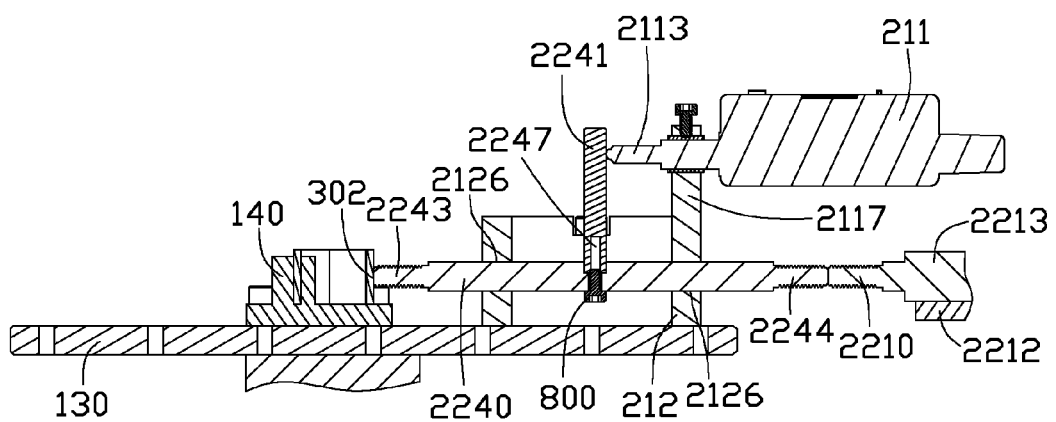
FIG. 4 is a sectional view of the deformation testing device taken along line IV-IV of FIG. 1.

Referring to FIGS. 3 and 4, the positioning device 140 includes a base plate 142 and a positioning portion 144 formed on the base plate 142. Four fifth threaded through holes 1422 are defined in four corners of the base plate 142. Four bolts 900 extend through the fifth threaded through holes 1422 and the fourth threaded through holes 132 to secure the positioning device 140 to the platform 130. The positioning portion 144 includes a first block 1441, a second block 1442 and a third block 1443. The first block 1441 is spaced apart from and substantially parallel to the second block 1442. The third block 1443 is spaced apart from and substantially perpendicular to the first block 1441 and the second block 1442. When the workpiece 300 is placed on the positioning device 140, an arm of the workpiece 300 is sandwiched between the first block 1441 and the second block 1442, a bent portion of the workpiece 300 abuts against the third block 1443 and the elastic arm 302 is free to move. When the shape of the workpiece 300 is different, the positioning device 140 may be changed accordingly. The location of the positioning device 140 on the platform 130 can be changed by fastening the positioning device 140 to different fourth threaded through holes 132 of the platform 130. The height of the positioning device 140 can be adjusted by rotating the knob 126 clockwise/counterclockwise. Therefore, it is convenient to adjust the workpiece 300 to a desirable position.

Referring to FIG. 3, the testing machine 200 includes a distance-measurement device 210 and a force-applying device 220. The distance-measurement device 210 includes a meter base 212 and a meter 211.

The meter base 212 includes a first sidewall 2121, a second sidewall 2122, a third sidewall 2123 and a fourth sidewall 2124. The first sidewall 2121 opposes the third sidewall 2123. The second sidewall 2122 opposes the fourth sidewall 2124. The first sidewall 2121, the second sidewall 2122, the third sidewall 2123 and the fourth sidewall 2124 are connected end-to-end and cooperatively form a receiving room 2120. Two sixth threaded through holes 2125 are defined in two respective upper sides of the first sidewall 2121 and the third sidewall 2123. Two second through holes 2126 are defined in the second sidewall 2122 and the fourth sidewall 2124, respectively. The two second through holes 2126 are aligned with each other. A support post 2127 extends from an upper side of the second sidewall 2122. A third through hole 2128 is defined in the support post 2127. A central axis of the third through hole 2128 is substantially parallel to that of the second through hole 2126. A seventh threaded through hole 2129 is defined in the top of the support post 2127. The seventh threaded through hole 2129 is in communication with the third through hole 2128. A central axis of the seventh threaded through hole 2129 is substantially perpendicular to that of the third through hole 2128. The meter base 212 is secured to the platform 130 by fastening bolts 902 into the sixth threaded through holes 2125 and the fourth threaded through hole 132.

The meter 211 includes a meter body 2111, a hollow cylinder 2112, a retractable measurement probe 2113 and a bushing 2144. The measurement probe 2113 extends from the meter body 2111 through the hollow cylinder 2112. A distance that the measurement probe 2113 moves can be displayed and be read on the meter body 2111. The bushing 2144 sleeves the hollow cylinder 2112 and is received in the third through hole 2128. A bolt 700 is screwed into the seventh threaded through hole 2129 to secure the bushing 2114 and the hollow cylinder 2112 on the support post 2127. Therefore, the meter 211 is secured to the meter base 212. In this embodiment, the meter 211 is a dial test indicator.

The force-applying device 220 includes a force-measurement device 221, a guide rail 222, an operation device 223 and a transmission member 224.

The force-measurement device 221 is slidably mounted on the guide rail 222. The force-measurement device 221 includes a force meter 2213 and a mounting plate 2212. The force meter 2213 is configured to apply and measure a pull force or a push force acted upon the elastic arm 302 of the workpiece 300. The force meter 2213 is secured to the mounting plate 2212. The force meter 2213 includes two second threaded posts 2210 extending from opposite sides thereof.

The guide rail 222 is secured to the support plate 112 and includes two passages 2220 opposing each other. Opposite ends of the mounting plate 2212 are slidably received in the two passages 2220, respectively. Therefore, the force meter 2213 together with the mounting plate 2212 is capable of sliding along the passages 2220.

The operation device 223 includes a support portion 2230 and a lever 2231. The support portion 2230 is secured on the support 110. The lever 2231 extends through the support portion 2230.

An eighth threaded through hole 2236 is defined in the support portion 2230. The lever 2231 includes a third threaded post 2232, a connecting post 2234 and a grip 2235. The third threaded post 2232 is screwed through the eighth threaded through hole 2236 and is secured to the mounting plate 2212. The connecting post 2234 securely connects the third threaded post 2232 and the grip 2235. When an operator grips the grip 2235 to rotate the lever 2231, the third threaded post 2232 rotates and moves along the eighth threaded through hole 2236, thereby driving the force-measurement device 221 to move along the passages 2220.

The transmission member 224 includes a horizontal post 2240 and a vertical post 2241 secured to the horizontal post 2240. The horizontal post 2240 includes a middle portion 2242, a first contact terminal 2243 and a second contact terminal 2244. The first contact terminal 2243 and the second contact terminal 2244 extend from opposite ends of the middle portion 2242, respectively. The first contact terminal 2243 and the second contact terminal 2244 each have an outer threaded circumference surface. A groove 2245 and a ninth threaded through hole 2246 are defined in the middle portion 2242 along a longitudinal axis of the vertical post 2241. The groove 2245 is in communication with the ninth threaded through hole 2246. The horizontal post 2240 moveably extends through the second through holes 2126 with the groove 2245 in the receiving room 2120. One end of the vertical post 2241 is received in the groove 2245. A threaded blind hole 2247 (see FIG. 4) is defined in the one end of the vertical post 2241. A bolt 800 is screwed into the ninth threaded through hole 2246 and the threaded blind hole 2247 to secure the vertical post 2241 to the horizontal post 2242. The measurement probe 2113 is in contact with and abuts against the vertical post 2241. The second contact terminal 2244 faces the second threaded post 2210 and may be in contact with the second threaded post 2210. The horizontal post 2240 is aligned with the second threaded post 2210 and is configured to transmit a force from the second threaded post 2210 to the elastic arm 302 of the workpiece 300.

When in use, the workpiece 300 is placed in the positioning device 140. The operator rotates the knob 126 to adjust the height of the workpiece 300 to position the workpiece 300 at a level where the horizontal post 2240 is. The operator grips the grip 2235 to rotate the lever 2231. Therefore, the force-measurement device 221 moves towards the workpiece 300. The transmission member 224 also moves towards the workpiece 300 as the second threaded post 2210 pushes the horizontal post 2240 of the transmission member 224. When the first contact terminal 2243 of the horizontal post 2240 just makes contact with the elastic portion 302 of the workpiece 300, the operator stops rotating the lever 2231. Then, the meter 211 and the force meter 2213 are zeroed.

Next, the operator grips the grip 2235 to rotate the lever 2231. Therefore, the horizontal post 2240 pushes the elastic portion 302 of the workpiece 300 and the elastic portion 302 is moved. A push force F1 is applied to the elastic portion 302 and is displayed on the force meter 2213. At the same time, the vertical post 2241 moves together with the horizontal post 2240 towards the workpiece 300 and the measurement probe 2113 is elongated as the vertical post 2241 moves. A distance L1 that the measurement probe 2113 moves is displayed and can be read on the meter body 2111. Therefore, the distance L1 is equal to the distance that the elastic portion 302 moves and can be regarded as the deformation of the workpiece 300 under the push force F1. Applying different push forces to the workpiece 300 can obtain a collection of deformations of the workpiece 300. Thus, a diagram of indicative relationship between the push force (pressure) and the deformation of the workpiece 300 can be obtained.

Figure 5:
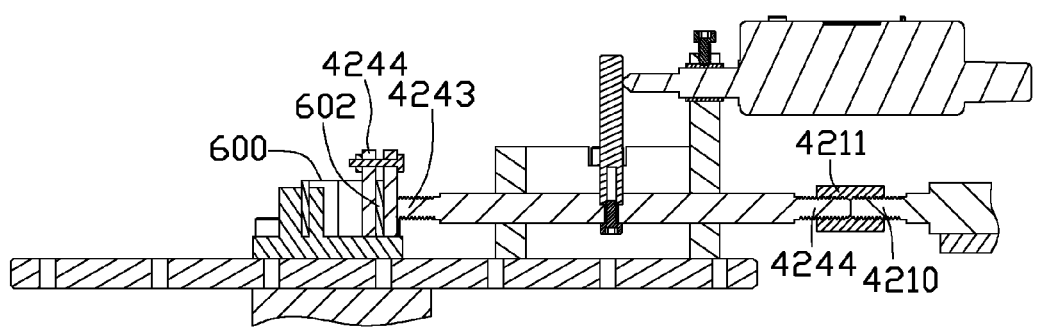
FIG. 5 is a sectional view of a deformation testing device according to a second embodiment.

Referring to FIG. 5, a deformation testing device 20, according to a second embodiment, is shown. Differences between the deformation testing device 20 and the deformation testing device 10 of the first embodiment are that a first contact terminal 4243 includes a clamp 4244 at one end of the first contact terminal 4243, and a second contact terminal 4244 is connected to a second threaded post 4210 using a hollow cylinder 4211 with an internally threaded circumference surface 4212. The clamp 4244 is configured to clamp an elastic portion 602 of a workpiece 600. Therefore, the deformation testing device 20 is suitable for applying a pull force to the elastic portion 602 of the workpiece 600 and a diagram of indicative relationship between pull forces and the deformation of the workpiece 300 can be obtained.

It is to be understood that, in alternative embodiments, if a diagram of indicative relationships between pull forces and the deformation of the workpiece 300 is needed, the first contact terminal may include hooks or the like to be connected to the workpiece 300, the second contact terminal, and the second threaded post may include hooks or the like to be connected to each other.

It is to be understood, however, that even though numerous characteristics and advantages of the present embodiments have been set forth in the foregoing description, together with details of the structures and functions of the embodiments, the disclosure is illustrative only, and changes may be made in detail, especially in matters of shape, size, and arrangement of parts within the principles of the disclosure to the full extent indicated by the broad general meaning of the terms in which the appended claims are expressed.

What is claimed is:

1. A deformation testing device, comprising:
a base configured to hold a workpiece, the workpiece comprising an elastic portion; and
a testing machine arranged on the base, the testing machine comprising:
a distance-measurement device configured to meter a moving distance of the elastic portion and comprising a meter base and a meter, the meter base secured to the base and comprising four sidewalls connected to each other end-to-end and a support post extending up from an upper side of one of the sidewalls, the four sidewalks cooperatively forming a receiving room, the meter comprising a retractable measurement probe; and
a force-applying device comprising a force meter and a transmission member, the force meter slidably mounted on the base and comprising a three-applying post, the transmission member comprising a first post and a second post, the first post moveably extending through the meter base, the first post aligned with the force-applying post and configured to transmit a force from the force-applying post to the elastic portion, the second post secured to and extending up from the first post and partially received in the receiving room, the meter mounted on the support post, the measurement probe extending through the support post and configured for abutting against the second post, the force meter configured to apply and measure a force acted upon the elastic portion through the force-applying post and the first post.

2. The deformation testing device of claim 1 wherein the base comprises a support and a position adjusting device, the support comprises a support plate and four feet arranged at respective four corners of the support plate, the position adjusting device comprises an insertion body and a moveable platform, the insertion body extends through the support plate, the position adjusting device is secured to the support plate, and the moveable platform is moveably received in the insertion body.

3. The deformation testing device of claim 2, wherein the meter further comprises a meter body, a hollow cylinder and a bushing, the meter body is configured to display the moving distance of the elastic portion, the hollow cylinder extends from the meter body, the bushing sleeves the hollow cylinder and is secured to the support post, and the measurement probe extends from the meter body through the hollow cylinder and moveably extends through the support post.

4. The deformation testing device of claim 3, wherein the four sidewalls comprise a first sidewall, a second sidewall, a third sidewall and a fourth sidewall connected end-to-end in that order, the support post extends from an upper side of the second sidewall, and the first post moveably extends through the second sidewall and the fourth sidewall.

5. The deformation testing device of claim 4, wherein the force-applying device further comprises a mounting plate, a guide rail, and an operation device, the guide rail is secured to the support plate and comprises two passages opposing each other, opposite ends of the mounting plate are slidably received in the two passages, respectively, the force meter is secured to the mounting plate, and the operation device comprises a support portion secured to the support plate and a lever rotatably extending through the support portion and secured to the mounting plate.

6. The deformation testing device of claim 5, wherein the lever comprises a threaded post, a connecting post and a grip, the threaded post threadedly extends through the support portion and is secured to the mounting plate, and the connecting post connects the threaded post and the grip.

7. The deformation testing device of claim 1, wherein the first post comprises a clamp at a first end thereof, and the clamp is configured to clamp the elastic portion.

8. The deformation testing device of claim 7, further comprising a hollow cylinder having an internally threaded circumference surface, wherein the first post further comprises an opposing, outwardly threaded second end, the force-applying post is outwardly threaded, and the first post is connected to the force-applying post by threaded engagement between the hollow cylinder, the second end of the first post and the force-applying post.

9. The deformation testing device of claim 2, wherein the support plate comprises a top surface and a bottom surface at opposite sides thereof, two protruding plates extend from opposite sides of the insertion body, the protruding plates are in contact with the bottom surface of the support plate and are secured to the bottom surface of the support plate, the moveable platform comprises an insertion portion and a mounting tray at a top end of the insertion portion, the insertion portion is moveably received in the insertion body, and the mounting tray is positioned above the top surface of the support plate.

10. The deformation testing device of claim 9, wherein the base further comprises a platform and a positioning device, the platform is secured to the mounting tray, the positioning device comprises a base plate and a positioning plate formed on the base plate, the base plate and the meter base are secured to the platform, the positioning, plate comprises a first block, a second block and a third block, the first block is spaced apart from and is substantially parallel to the second block, and the third block is spaced apart from and is substantially perpendicular to the first block and the second block.

11. The deformation testing device of claim 9, wherein the position adjusting device further comprises a threaded post, a secured plate, two nuts and a knob, the threaded post comprises a post body and a flange, the post body comprises a first threaded portion, a second threaded portion and an engaging portion in that order from a top to a bottom of the post body, the flange is mounted on the post body and is located between the first threaded portion and the second threaded portion, the secured plate is mounted to a bottom of the insertion body, the post body is received in the insertion body, the flange abuts against a top surface of the secured plate, the first threaded portion is threadedly engaged with the insertion portion, the second threaded portion extends through the secured plate and is threadedly engaged with the two nuts, and the engaging portion is engaged with the knob.

12. The deformation testing device of claim 4, wherein two through holes are defined in the second sidewall and the fourth sidewall, respectively, and are aligned with each other, a threaded through hole is defined in a top of the support post and a through hole is defined in the support post with the threaded through hole communicating with the through hole, the first post extends through the two through holes of the second sidewall and the fourth sidewall, a central axis of the through hole of the support post is substantially parallel to central axes of the two through holes of the second sidewall and the fourth sidewall, and the bushing is received in the through hole of the support post and is secured to the support post by a bolt screwed into the threaded through hole and engaged with the bushing.

13. The deformation testing device of claim 12, wherein the first post comprises a middle portion, a first contact terminal and a second contact terminal, the first contact terminal and the second contact terminal extend from opposite ends of the middle portion, respectively, the first contact terminal and the second contact terminal extend through the second sidewall and the fourth sidewall, respectively, a groove is defined in the middle portion and is received in the receiving room, and the second post is secured in the groove by a bolt.

14. The deformation testing device of claim 13, wherein the first post is substantially perpendicular to the second post.

15. The deformation testing device of claim 8, wherein the meter further comprises a meter body, a hollow cylinder and a bushing, the meter body is configured to display the moving distance of the elastic portion, the hollow cylinder extends from the meter body, the hushing sleeves the hollow cylinder and is secured to the support post, and the measurement probe extends from the meter body through the hollow cylinder and moveably extends through the support post.

16. The deformation testing device of claim 15, wherein the four sidewalls comprises a first sidewall, a second sidewall, a third sidewall and a fourth sidewall connected end-to-end in that order, the support post extends from an upper side of the second sidewall, and the first post moveably extends through the second sidewall and the fourth sidewall.

17. The deformation testing device of claim 16, wherein two through holes are defined in the second sidewall and the fourth sidewall, respectively, and are aligned with each other, a threaded through hole is defined in a top of the support post and a through hole is defined in the support post with the threaded through hole communicating with the through hole, the first post extends through the two through holes of the second sidewall and the fourth sidewall, a central axis of the through hole of the support post is substantially parallel to central axes of the two through holes of the second sidewall and the fourth sidewall, and the bushing is received in the through hole of the support post and is secured to the support post by a bolt screwed into the threaded through hole and engaged with the bushing.

18. The deformation testing device of claim 17, wherein the first post comprises a middle portion, a first contact terminal and a second contact terminal, the first contact terminal and the second contact terminal extend from opposite ends of the middle portion, respectively, the first contact terminal and the second contact terminal extend through the second sidewall and the fourth sidewall, respectively, a groove is defined in the middle portion and is received in the receiving room, and the second post is secured in the groove by a bolt.

19. The deformation testing device of claim 18, wherein the first post is substantially perpendicular to the second post.

* * * * *